(12) United States Patent
Clemente et al.

(10) Patent No.: US 12,186,051 B2
(45) Date of Patent: Jan. 7, 2025

(54) SYSTEMS AND METHODS FOR DETERMINING AND COMMUNICATING LEVELS OF BILIRUBIN AND OTHER SUBCUTANEOUS SUBSTANCES

(71) Applicant: Bilibaby, LLC, Phoenixville, PA (US)

(72) Inventors: Matthew James Clemente, San Jose, CA (US); George Stavis, Dobbs Ferry, NY (US); Robert Stavis, Bryn Mawr, PA (US); Mary Elizabeth Lemma, West Chester, PA (US); Steven P. Getz, Malvern, PA (US)

(73) Assignee: Bilibaby, LLC, Phoenixville, PA (US)

( * ) Notice: Subject to any disclaimer, the term of this patent is extended or adjusted under 35 U.S.C. 154(b) by 0 days.

(21) Appl. No.: 17/897,108

(22) Filed: Aug. 26, 2022

(65) Prior Publication Data

US 2023/0069111 A1     Mar. 2, 2023

Related U.S. Application Data

(60) Provisional application No. 63/238,058, filed on Aug. 27, 2021.

(51) Int. Cl.
*A61B 5/00* (2006.01)
*A61B 5/1455* (2006.01)
*G16H 40/67* (2018.01)

(52) U.S. Cl.
CPC .......... *A61B 5/0022* (2013.01); *A61B 5/1455* (2013.01); *G16H 40/67* (2018.01)

(58) Field of Classification Search
CPC ..... A61B 5/0022; A61B 5/1455; G16H 40/67
See application file for complete search history.

(56) References Cited

U.S. PATENT DOCUMENTS 2,437,916 A    3/1948  Greenwald
5,259,382 A *  11/1993 Kronberg
(Continued)

FOREIGN PATENT DOCUMENTS

CN    103340604 A    10/2013
WO    2008039299 A2   4/2008
(Continued)

OTHER PUBLICATIONS

Jaundice Meter (JM-103) User Manual, Konica Minolta and Hill-Rom Air-Shields (Oct. 2003).
(Continued)

*Primary Examiner* — Jessica Lemieux
*Assistant Examiner* — William T. Monticello
(74) *Attorney, Agent, or Firm* — Pryor Cashman LLP

(57) ABSTRACT

A system including a computing device, a software application stored in a memory of the computing device and configured to run on a processor of the computing device, and a module in communication with the computing device, said module including a data communication capability, where the data includes light intensity or wavelength information, a light source configured to provide light capable of penetrating the patient's skin to a subcutaneous level, a light sensor configured to detect the light from the light source reflected and scattered from the patient's skin including from the subcutaneous level at a single point in time or sequentially at multiple points in time, and a power source, where the software application is configured to determine levels or concentrations of a substance in a patient's skin based on a measurement of light intensity or wavelength from the light sensor.

17 Claims, 5 Drawing Sheets

(56) References Cited

U.S. PATENT DOCUMENTS

| | | |
|---|---|---|
| 9,934,589 B2 | 4/2018 | Clemente et al. |
| 2002/0095077 A1 | 7/2002 | Swedlow et al. |
| 2003/0011773 A1 | 1/2003 | Dick |
| 2010/0179469 A1* | 7/2010 | Hammond et al. |
| 2010/0185064 A1* | 7/2010 | Bandic et al. |
| 2011/0245637 A1* | 10/2011 | McKenna |
| 2012/0203086 A1* | 8/2012 | Rorabaugh et al. |
| 2013/0023742 A1* | 1/2013 | Molcho et al. |
| 2013/0057865 A1* | 3/2013 | Meijer et al. |
| 2013/0273524 A1 | 10/2013 | Ehrenkranz |
| 2013/0296673 A1 | 10/2013 | Thaveeprungsriporn et al. |
| 2014/0018647 A1 | 1/2014 | Segman |
| 2014/0316226 A1 | 10/2014 | Ferber et al. |
| 2014/0323832 A1* | 10/2014 | Thangaraj et al. |
| 2016/0012610 A1* | 1/2016 | Clemente et al. |
| 2017/0281877 A1* | 10/2017 | Marlin et al. |
| 2019/0008432 A1* | 1/2019 | Bashan et al. |
| 2020/0018640 A1* | 1/2020 | Bonitatibus et al. |
| 2021/0089814 A1 | 3/2021 | Lopes et al. |
| 2021/0236844 A1* | 8/2021 | Jain et al. |
| 2022/0015673 A1* | 1/2022 | Gruber |

FOREIGN PATENT DOCUMENTS

| | | |
|---|---|---|
| WO | 2013096766 A2 | 6/2013 |
| WO | 2013160780 A1 | 10/2013 |
| WO | 2015153913 A1 | 10/2015 |
| WO | 2016027274 A1 | 2/2016 |
| WO | 2016047754 A1 | 3/2016 |

OTHER PUBLICATIONS

International Search Report in PCT Application No. PCT/US2022/041763 (Nov. 23, 2022).

Written Opinion of the International Searching Authority in PCT Application No. PCT/US2022/041763 (Nov. 23, 2022).

* cited by examiner

SYSTEMS AND METHODS FOR DETERMINING AND COMMUNICATING LEVELS OF BILIRUBIN AND OTHER SUBCUTANEOUS SUBSTANCES

RELATED APPLICATIONS

This application claims priority to U.S. Provisional Patent Application No. 63/238,058, filed Aug. 27, 2021, the disclosure and teachings of which are incorporated herein by reference.

FIELD OF THE INVENTION

The present invention relates generally to systems and methods for determining concentrations of a substance in a patient's body based on the coloration of the patient's skin. The invention provides a module with light sources and optical detectors coupled to a computing device, such as a smartphone, to measure the substance's optical properties in the skin, calculate the concentration of the substance in the skin, analyze the data with respect to accepted clinical guidelines, and then electronically communicate the information to patients, caregivers, and/or health care providers.

BACKGROUND OF THE INVENTION

During the first weeks of life, most newborns develop a visible yellow coloring of the skin, known as jaundice, due to an increase in a chemical called bilirubin. Moderate levels of bilirubin are benign, but very high levels—called severe hyperbilirubinemia—can cause a condition called kernicterus, which is a severe and life-long severe form of athetoid cerebral palsy with hearing dysfunction, dental-enamel dysplasia, and intellectual handicaps.

In order to reduce the likelihood of kernicterus, the American Academy of Pediatrics recommends that all infants be evaluated for jaundice with systematic measurement of bilirubin and treated according to specific protocols. Measurement of bilirubin levels is most accurately done by chemical analysis of a blood specimen, but hand-held instruments have also been developed to estimate bilirubin levels by optical measurement of subcutaneous skin coloration. Because of their high cost, such instruments are only practical in a hospital, clinic, or doctor's office setting. There are no currently available technologies for estimating the bilirubin level using a device available at a price level consistent with use in the home. Accordingly, it is often necessary for infants to return to a laboratory facility or hospital to have a blood sample obtained to determine bilirubin levels, which may involve substantial inconvenience and cost.

The present invention described herein provides a low-cost hand-held module (the "module") which utilizes the functions of smartphones, tablets, computers, or other personal devices with communication capabilities to give parents and healthcare providers a noninvasive, rapid, and easy-to-use tool to monitor bilirubin through changes in the subcutaneous skin coloration of the infant. The invention further provides an affordable method of estimating bilirubin levels in the home that will simplify and vastly improve the outpatient management of hyperbilirubinemia in babies during the first weeks at home. Moreover, the technology of optical measurement of color wavelengths and light intensity utilized in the present invention may also be extended to the measurement of other bodily substances.

SUMMARY OF THE INVENTION

The present invention provides systems and methods for determining levels of bilirubin or other substances in an individual based on subcutaneous skin coloration. The module described herein includes light sources and light detectors which may connect by wireless or wired communication to certain hardware, such a smartphone, tablet, or other mobile or stationary computing device (e.g., laptop computer or desktop computer) (collectively, the "hardware"), and further utilizes this hardware to analyze the data with respect to widely accepted clinical guidelines and communicate the calculated levels and recommended actions to health care providers for appropriate evaluation and actions. In another embodiment, the relevant hardware functions may be contained within the module, so that it becomes a standalone solution for the determination of bodily substances based on the optical properties of the substance.

The module may include light sources emitting either specific wavelengths of light (e.g., blue and green wavelengths for bilirubin measurements) or white light to penetrate the skin to the subcutaneous level.

If specific wavelengths of light are emitted by the light source, one or more light sensors measure the light level intensities and wavelengths scattered and reflected from the subcutaneous skin layer.

If white light is emitted, the white light scattered and reflected from the subcutaneous skin layer shall be separated into separate wavelengths of light by filters, photodiodes, or other components and measured for the light level intensity for the desired wavelength (e.g., blue and green wavelengths for bilirubin).

By use of an algorithm in the firmware or software in the module or the hardware, the coloration of the subcutaneous tissue may be determined which, in turn, identifies the concentration of substances, such as bilirubin, in the subcutaneous tissues.

In a preferred embodiment, the remote module may also include a wireless communication device, such as a BLUETOOTH transceiver or communication device, or a wired connection to send information to the hardware about the scattered and reflected light level intensities and wavelengths measured by one or more sensors. The remote module may also include a battery or other power source, such as a wired power source.

The hardware may include wireless and/or wired capabilities to receive data containing information about the light level intensities and wavelengths measured by the light sensor or sensors in the module. The hardware may also include an application or other software system to calculate and/or display bilirubin values, provide graphical and/or analytic evaluations of the concentration of bilirubin or other optically determinable substances in accordance with established clinical guidelines, and/or provide a graphical or analytic display of the values obtained by the present invention compared to clinical standards (the "app"). The hardware may also include capabilities to control and to display information on the remote module and to transmit information derived from the application or other software and other relevant parameters to the user and/or health care providers by any and all systems designed for the secure transmission of health care information. In another embodiment, the module may refer to a combination of the remote module and the hardware in a single housing, operating as a standalone device.

In general, in one aspect, the invention features a system for monitoring and communicating levels or concentrations of a substance in a patient's skin based on an optical property of the substance, including a computing device including a memory and a processor, a software application stored in the memory of the computing device and configured to run on the processor of the computing device, and a module in communication with the computing device, said module including a data communication capability, where the data includes light intensity or wavelength information, a light source configured to provide light capable of penetrating the patient's skin to a subcutaneous level, a light sensor configured to detect the light from the light source reflected and scattered from the patient's skin including from the subcutaneous level at a single point in time or sequentially at multiple points in time, and a power source, where the software application is configured to determine the levels or concentrations of the substance in the patient's skin based on a measurement of light intensity or wavelength from the light sensor.

Implementations of the invention may include one or more of the following features. The light sensor may measure light intensity sequentially at multiple points in time in rapid succession. The light source may be configured to provide blue and green wavelength light. The light source may be configured to provide white light, where the module may further include a photodiode or a light filter to separate the white light reflected and scattered from the patient's skin into blue and green wavelength light. The light sensor may measure light intensity at a single location on the patient's skin or at multiple locations on the patient's skin. The power source may be a battery or a wired power source.

The substance may be bilirubin. The substance may also be a bodily fluid, a body product, a drug marked for a color marker, a drug containing a color marker, a biologic marked for a color marker, or a biologic containing a color marker. The system may further include an ambient light sensor, where the software application may be configured to account for light intensity of ambient light measured from the ambient light sensor in calculating a net light intensity of light reflected and scattered from the patient's skin. The software application may be configured to measure a light intensity of a wavelength of light present in one or more readings captured by the light sensor. The software application may be configured to transmit or display the levels or concentrations of the substance in the patient's skin to a recipient, where the recipient may be the patient, a user of the system, a caregiver, health care providers, or a secure website. The software application may be configured to store a result of system use and provide a comparison of the result with clinical standards.

In general, in another aspect, the invention features a system for monitoring and communicating levels or concentrations of a substance in a patient's skin based on an optical property of the substance, including a computing device including a memory and a processor, a software application stored in the memory of the computing device and configured to run on the processor of the computing device, and a module in communication with the computing device, said module including a data communication capability, where the data includes light intensity or wavelength information, a light source configured to provide light capable of penetrating the patient's skin to a subcutaneous level, a light sensor configured to detect the light from the light source reflected and scattered from the patient's skin including from the subcutaneous level at a single point in time or sequentially at multiple points in time, a skin sensor located on the module at a region configured to contact the patient's skin, and a power source, where the software application is configured to determine the levels or concentrations of the substance in the patient's skin based on a measurement of light intensity or wavelength from the light sensor, and where the skin sensor is configured to determine whether there is a light-tight seal or sufficient pressure between the module and the patient's skin.

Implementations of the invention may include one or more of the following features. The skin sensor may include a spring-biased electromechanical switch, an optical sensor, or a capacitive or piezo-electric sensor that detects tissue proximity or pressure. The system may further include an indicator light or a visual display activated by the skin sensor to indicate whether there is a light-tight seal or sufficient pressure between the module and the patient's skin. The skin sensor may be configured to prevent operation or functioning of the system in the absence of a light-tight seal or sufficient pressure between the module and the patient's skin.

In general, in another aspect, the invention features a system for monitoring and communicating levels or concentrations of a substance in a patient's skin based on an optical property of the substance, including a computing device including a memory, a processor, and a communication capability, a software application stored in the memory of the computing device and configured to run on the processor of the computing device, and a module capable of operating separated and detached from the computing device, said module including a wireless or wired data communication capability, where the data includes light intensity or wavelength information, a light source configured to provide light capable of penetrating the patient's skin to a subcutaneous level, a light sensor configured to detect the light from the light source reflected and scattered from the patient's skin including from the subcutaneous level, and a power source, where the software application is configured to determine the levels or concentrations of the substance in the patient's skin based on a measurement of light intensity or wavelength from the light sensor of the remote module.

Implementations of the invention may include one or more of the following features. The computing device may be a smartphone or a tablet. The computing device may also be a laptop computer or a desktop computer. The wireless or wired data transmission capability may include BLUETOOTH or other wireless communication.

DETAILED DESCRIPTION OF THE INVENTION

A detailed description will now be given of the invention, including with reference to the attached FIGS. 1-4. It should be understood that these Figures are exemplary in nature and in no way serve to limit the scope of the invention. Other relevant teachings are found in U.S. Pat. No. 9,934,589, the disclosure of which is incorporated herein by reference.

The present invention describes systems and methods for measuring the level of bilirubin or other substances in a patient based on the subcutaneous skin coloration by using known light sources to generate scattered and reflected light from the subcutaneous skin layer. The systems and methods measure the light level intensities and wavelengths of several colors of scattered and reflected light and, based on an algorithm, calculate the concentration of bilirubin or other substances. The calculated bilirubin or other substance value is then displayed to the user and/or manually or automatically forwarded by any system designed for the secure transmission of health care information to relevant health care providers for clinical evaluation. The systems and methods employ one or more optical sensors 70 for obtaining tissue or other coloration-determined properties based on the emissions of known light sources 60 and the sensing of scattered and reflected light intensities and wavelengths caused by tissue interactions. The difference in the light intensities and wavelengths reflected from the subcutaneous skin layers allows the effect of the surface skin layer to be removed through analysis, and values for bilirubin or other substances in the subcutaneous layer may be calculated. In addition to bilirubin, relevant substances include but are not limited to other bodily fluids, body products, drugs and biologics marked for color markers, and drugs and biologics containing color markers.

Figure 1:
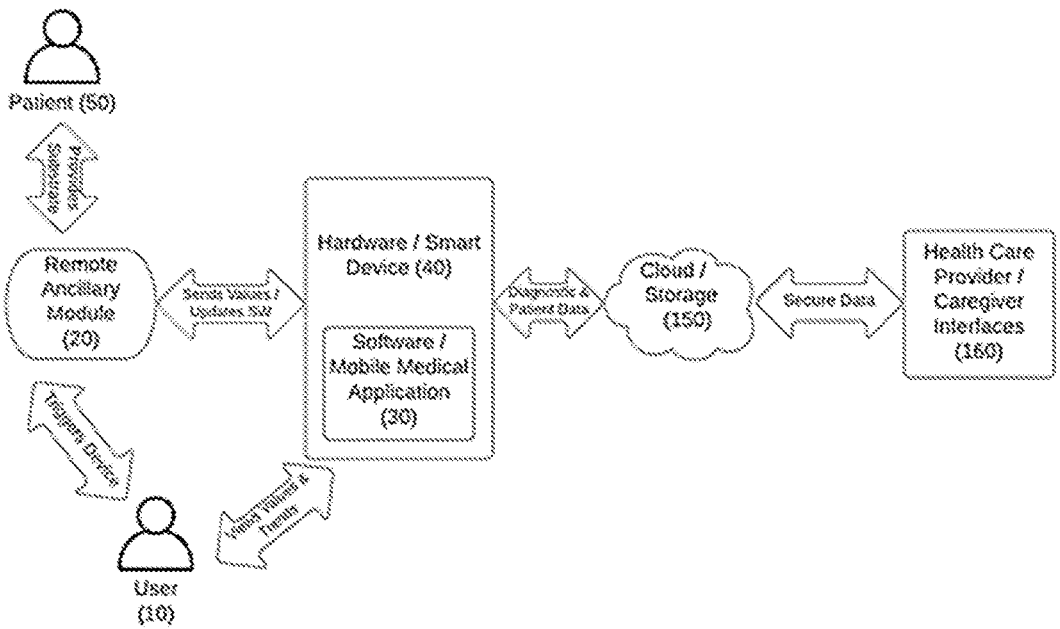
FIG. 1 is a diagram depicting the entire system architecture of an embodiment of the present invention.

At the highest level, such as shown in the illustration of FIG. 1, the invention includes a user 10, a patient 50 (who may or may not be the same person as user 10), hardware 40 (such as a smartphone, tablet, or computer), a software application 30, and a module 20 as exemplified in FIGS. 2 and 3A-3C.

To use the system, a user places the module 20 onto the patient's skin, typically on the forehead or over the sternum for newborn infant bilirubin applications, and activates the module with either a button or switch 140 or a skin detector/sensor acting as a switch 80. This causes the module 20 to emit light at specified wavelengths 60, which may be accomplished by one or more LEDs capable of issuing one or multiple colors simultaneously or sequentially in rapid succession. For embodiments relating to bilirubin, one color may be a blue wavelength light and another color may be a green wavelength light emitted into the subcutaneous skin layer. The emitted light 60 strikes the cutaneous tissues of the patient 50. A fraction of the incident energy is reflected at the tissue boundary, and a fraction is transmitted inside the tissue. A portion of the transmitted light from the subcutaneous skin layer is further absorbed, and then scattered and reflected by the tissue. The light distribution in the tissue is affected by the refractive index and absorption scattering characteristics of the tissue. The scattered and reflected light is then transmitted through single or multiple optical pathways to the module, and the light intensities of the specified wavelengths are detected by optical sensor 70, which may be an RGB sensor or two photodiodes, which may detect and separate the emitted light into separate colors, and which may measure different skin areas. In the preferred embodiment, the module may operate the emission of two or more light sources at different wavelengths at the same moment or sequentially in rapid succession, and also measure the intensity of the scattered and reflected light in more than one subcutaneous skin area. Averaging the values of the detected intensities of several scattered and reflected light emissions in different skin areas may increase the accuracy of the result. Similarly, other algorithms may utilize measurement pathways through multiple tissue thicknesses to negate the effects and variations of specific cutaneous properties of individuals from impacting the measurement of the target substance. In all cases where the hardware is external to the module, the optical sensors in the module may transmit the data related to the scattered and reflected light values by a wireless communication component 130 or wired connection to hardware 40, and the software or mobile application 30 either on the hardware 40 and/or firmware on the module 20 uses this data to calculate the level of bilirubin or other substance in the patient and display the result either on the module and/or the hardware. Where the hardware is contained within the module, the process is the same with the hardware directly connecting to the functions of the module.

Figure 4A:
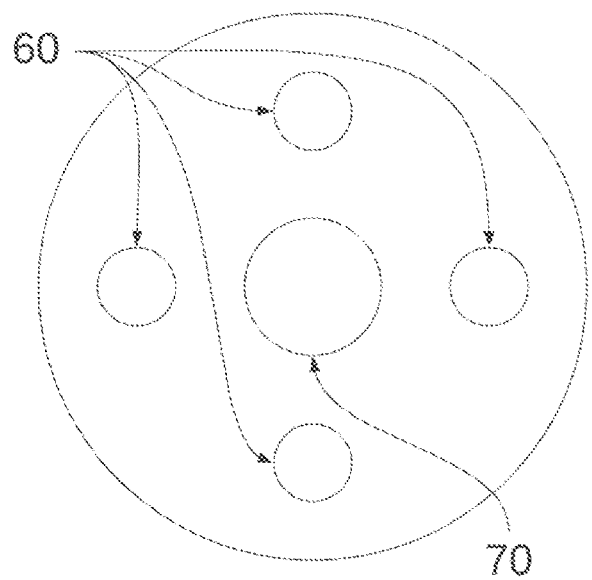
FIG. 4A provides an example of light emitters and sensors for inclusion in embodiments of the present invention.
Figure 4B:
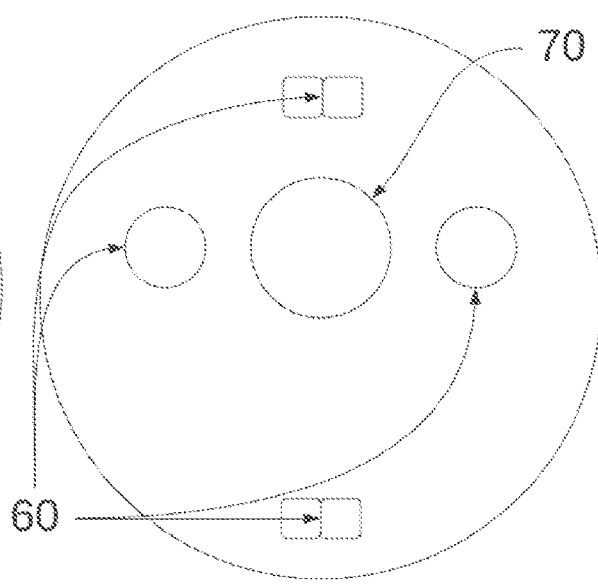
FIG. 4B provides another example of light emitters and sensors for inclusion in embodiments of the present invention.
Figure 4C:
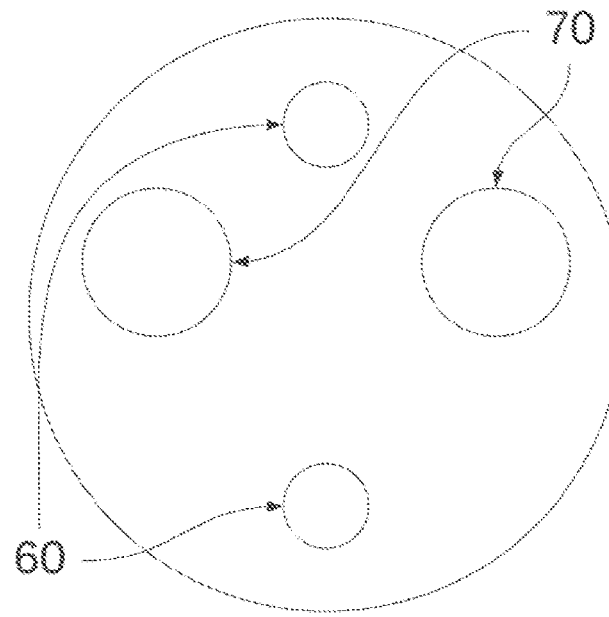
FIG. 4C provides another example of light emitters and sensors for inclusion in embodiments of the present invention.

FIGS. 4A-4C provide several illustrations of arrangements of light emitters and sensors that may be utilized in connection with the present invention.

The detailed description elaborates the methods by which the module 20 and the accompanying software or mobile application 30 will interface between the hardware 40 and the patient 50. The safety features and methods by which the module and the software or application reduce the possibility of errors in the use of the module are also described.

Although certain preferred embodiments of the invention utilize a module connected to the hardware by wireless or wired communication, another embodiment may combine the module and the hardware into a single unit, eliminating the separate wire or wireless communications between the two elements and retaining all of the additional elements described herein.

As seen in the Figures, the system includes hardware 40, such as a smartphone, computer, tablet, or other computing device, and module 20. The hardware 40 provides: (1) a user interface; (2) software or an application to convert the wavelengths and light intensities data measured by the sensor in the module 20 into a standard numerical reading of the concentration of bilirubin or other substance; and (3) a communication function to manually or automatically send the results for evaluation by a health care provider 160. The hardware 40 may also sent the standard numerical reading of the concentration of bilirubin or other substance to module 20 for display on a screen 100. In a preferred embodiment, the hardware is a smartphone, although tablets, personal computers, and other electronics may function for these purposes as well.

In some preferred embodiments, the hardware 40 may control the module 20, while in other embodiments, the module 20 may be activated by the skin detector on the module, acting as a switch, or directly by the patient 50 with a button or switch 140. The hardware 40 and/or the module 20 may also contain memory, such as storage and cloud access 150, for storing software and data, a processor to execute the software, and communication capabilities, such as wireless (e.g., BLUETOOTH, WI-FI, and the like) or wired communication capabilities.

The software or application 30 connects various aspects of the invention and allows the user to interact with the controls as well as visualize outputs of the analysis. The software in some embodiments may receive the input from the module to ensure the module is appropriately contacting the skin substrate by a skin detector/sensor 80. In the event the module is not in proper contact with the skin, the skin detector may prevent system operation until a proper contact can be obtained. In other embodiments, the skin detector might provide visual, audible or tactile feedback to the user until the appropriate skin contact is achieved. Once the software (or firmware in the module) obtains the relevant data, the input from one or more optical sensors can be used to calculate concentrations of substances, such as bilirubin, within the subcutaneous layer. The software or firmware may include an algorithm that separates and analyzes the output from the module to negate the effects of ambient light. The module may include an ambient light sensor to assist in this regard, namely by permitting the software or firmware to account for light intensity of ambient light as measured by the ambient light sensor in calculating a net light intensity of light scattered and reflected from the patient's skin. Additionally, the software may store these concentration values in each or both of the module and/or the hardware. Values may be stored in a memory in the module and/or may be used without immediate connection to the hardware in remote locations, so that the module may later be connected to the hardware for additional analysis and communication. The stored values may provide a logged history available to the user, the patient, caregivers, healthcare providers, electronic health records, and/or privacy-approved websites, such as a HIPAA-compliant website, either directly or through wireless communications. The stored values will assist in monitoring changes and/or trends and in providing clinical recommendations. This can be done automatically in real time, at regular intervals, or only when requested or approved by the user, such as by way of a pop-up window, audio signal, automated phone call, or otherwise. The software 30 may further provide reminders to the user to activate the present invention on a schedule. For example, the software 30 may alert a user if a reading was not taken according to a schedule. In some embodiments, the software 30 will report device errors.

Figure 3A:
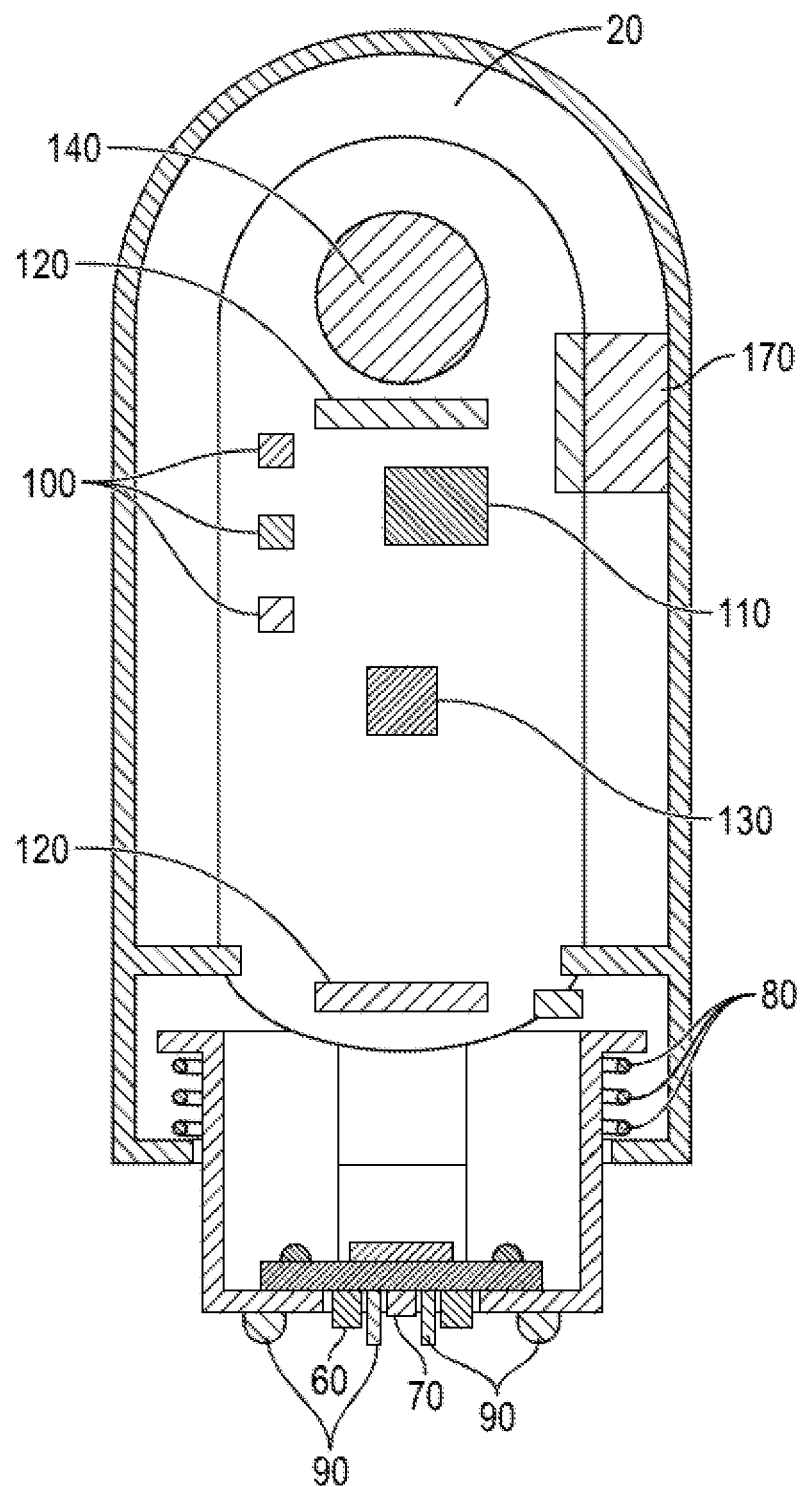
FIG. 3A provides a cross sectional view of the module of the present invention.
Figure 3B:
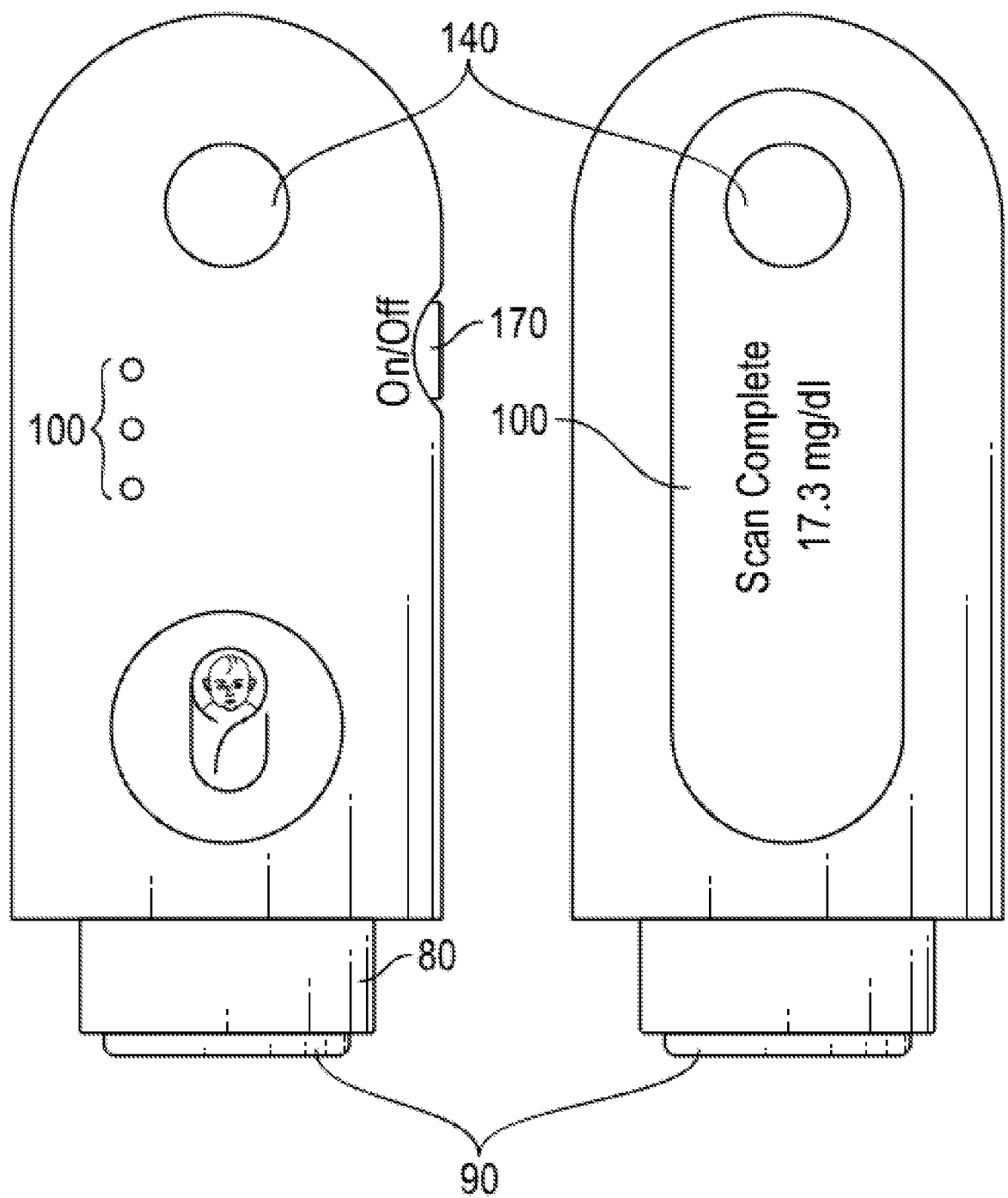
FIG. 3B provides a side view of the module of the present invention.
Figure 3C:
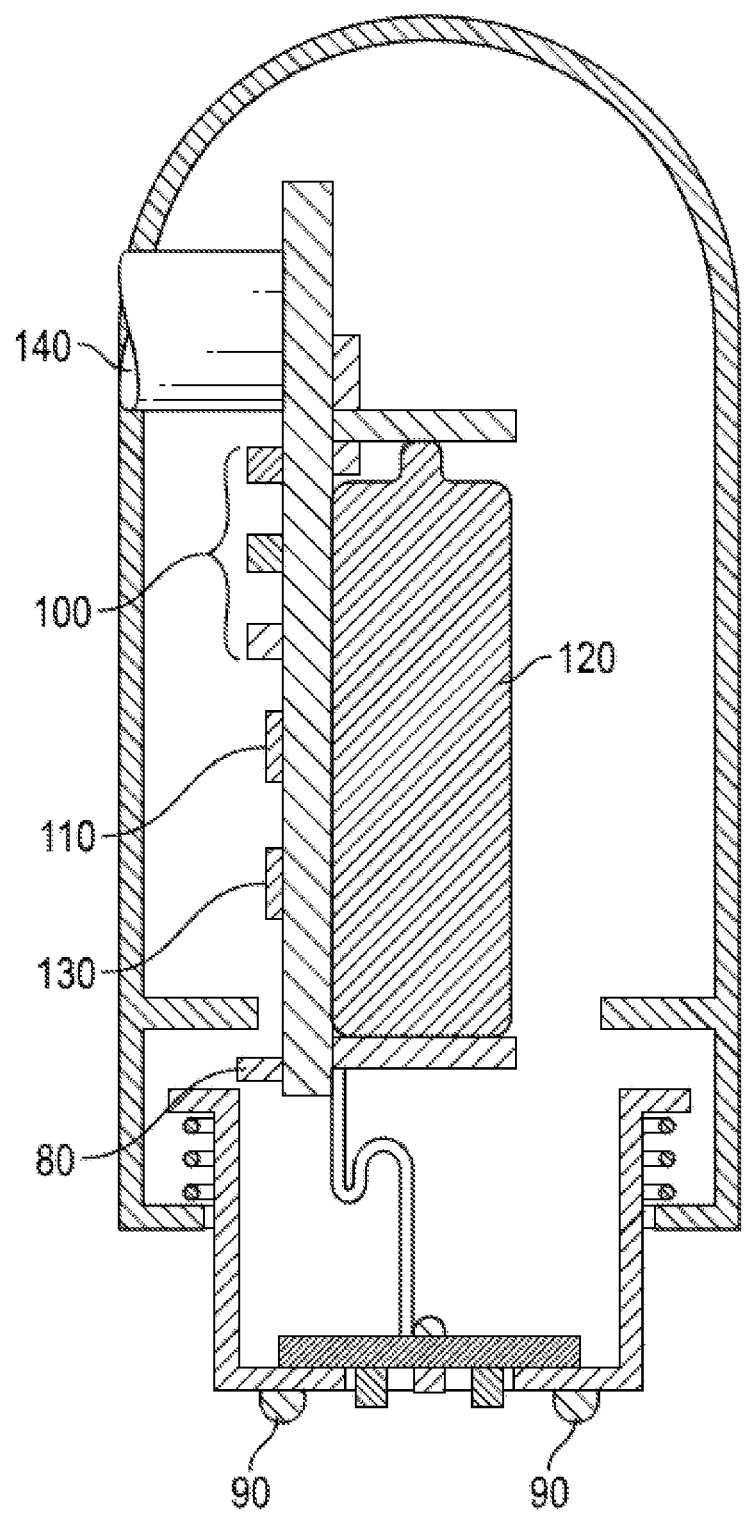
FIG. 3C provides a cross sectional view of the module of the present invention.

The module 20, as exemplified by FIGS. 3A-3C, may have its own microcontroller 110 and power supply 120. The module 20 may further include light sources, optical sensors, and wireless or wired data transmission or communication capabilities, such as a wireless communication processor 130 and/or a wire plug-in connection with the hardware 40. The module 20 may include a skin detector/sensor 80, light gaskets 90, and a status indicator or screen 100 to confirm that an appropriate connection to the skin exists, such that the device is light-tight when in skin contact and does not excessively deform the skin, either of which may result in incorrect readings. A second light gasket may prevent light leakage from the light sources to the optical sensors. The module may also have an on/off power switch 170 to manage power usage. The module may be activated by an activation button or switch 140, with such switching function being in the skin detector/sensor 80. As previously noted, embodiments of the present invention also include the incorporation of both the hardware and the module into a single unit.

Figure 2:
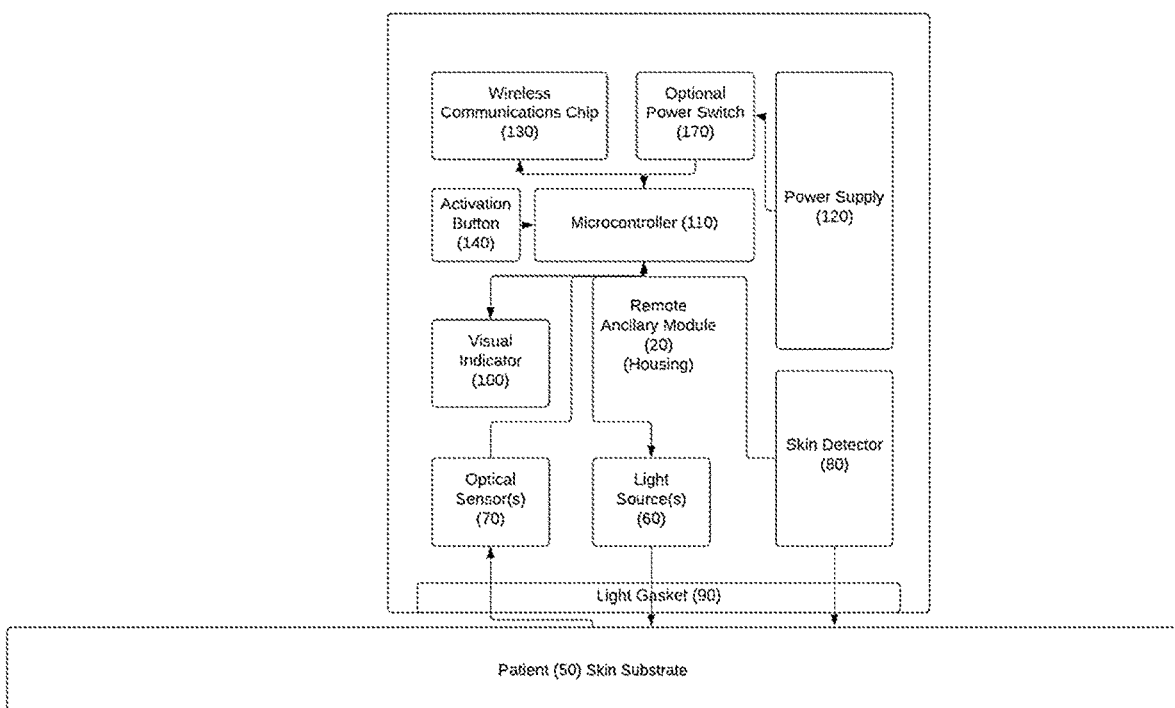
FIG. 2 is a diagram depicting the system architecture of an embodiment of the module of the present invention.

In greater detail relating to FIG. 2, the skin detector/sensor 80 and the light gaskets 90 are located by the skin contact area of the module 20. These devices provide the appropriate pressure range and ability to obstruct ambient light sources, such that the module 20 is properly sealed and ready for use. The skin detector/sensor 80 may be operated by a proximity, pressure, optical, or other sensor, such as an electromechanical, capacitive/piezo-electric, or optical switch. The electromechanical mechanism may include a spring-biased articulating mechanism in conjunction with a microswitch within the housing, which allows axial or rotational movement. When the user places the module 20 on the patient's skin, a compliant annular seal or seals, namely light gaskets 90, to perform two functions—keeping both ambient light and emitted light 60 from reaching the optical sensor 70. The status indictor or screen 100 could provide visual, audible, or tactile confirmation that the module is ready for operation. For example, visual confirmation by the status indicator or screen 100 may include activation of colored lights or other visual indicators, indicating by color or other means whether pressure and light-tightness standards, as measured by the skin detector/sensor 80, are met. The colored lights may be, for example, green (correct or ready for use), red (incorrect), or blue (test complete). If there is an improper connection or contact between the skin and the module, status indicator or screen 100 via skin detector/sensor 80 may prevent operation of the module until an acceptable or sufficient range of pressure against the skin or light-tightness seal is maintained.

The module 20 may also have voids, gaps, or additional light pathways or pipes to allow additional sensors, such as an ambient light sensor, to have direct or indirect access to external light sources that would also influence the tissue properties and permit incorporation into software algorithms.

The invention can be used in a multitude of embodiments, including those described herein. Although each embodiment is described through systems and methods most optimal for that particular embodiment, the systems and methods disclosed can be combined or used in parallel with other embodiments disclosed or envisioned.

The embodiments and examples above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of this disclosure. For a better understanding of the invention, its operating advantages and the specific objects attained by its uses, reference should be had to the accompanying drawings and descriptive matter in which there are illustrated exemplary embodiments of the invention.

What is claimed is:

1. A system for determining levels or concentrations of a substance in a patient's skin based on an optical property of the substance, comprising:
    a computing device comprising a memory and a processor;
    a software application stored in the memory of the computing device and configured to run on the processor of the computing device; and
    a module in communication with the computing device and separated and detached from the computing device, said module comprising:
        a data communication capability, wherein the data includes light intensity or wavelength information;
        a status indicator that provides visual, audible, or tactile confirmation that the module is ready for operation;
        two or more light sources that provide light which penetrates the patient's skin to a subcutaneous level, wherein the two or more light sources are configured to provide different wavelengths of light sequentially at multiple points in time in rapid succession;
        multiple optical pathways that transmit the light from the two or more light sources that is reflected and scattered from the patient's skin from the subcutaneous level to one or more light sensors that detect the light from the two or more light sources that is reflected and scattered from the patient's skin from the subcutaneous level sequentially at multiple points in time in rapid succession;
an ambient light sensor; and
a power source;
wherein the software application is configured to determine the levels or concentrations of the substance in the patient's skin based on a measurement of light intensity or wavelength from the light sensor, and
wherein the software application is configured to account for light intensity of ambient light measured from the ambient light sensor in calculating a net light intensity of light reflected and scattered from the patient's skin.

2. The system of claim 1, wherein the two or more light sources are configured to provide blue and green wavelength light.

3. The system of claim 1, wherein the two or more light sources are configured to provide white light, and wherein the module further comprises a photodiode or a light filter to separate the white light reflected and scattered from the patient's skin into blue and green wavelength light.

4. The system of claim 1, wherein the one or more light sensors measure light intensity at a single location on the patient's skin or at multiple locations on the patient's skin.

5. The system of claim 1, wherein the power source is a battery or a wired power source.

6. The system of claim 1, wherein the substance is bilirubin.

7. The system of claim 1, wherein the substance is a bodily fluid, a body product, a drug marked for a color marker, a drug containing a color marker, a biologic marked for a color marker, or a biologic containing a color marker.

8. The system of claim 1, wherein the software application is configured to measure a light intensity of a wavelength of light present in one or more readings captured by the one or more light sensors.

9. The system of claim 1, wherein the software application is configured to transmit or display the levels or concentrations of the substance in the patient's skin to a recipient, and wherein the recipient is the patient, a user of the system, a caregiver, health care providers, or a secure website.

10. The system of claim 1, wherein the software application is configured to store a result of system use and provide a comparison of the result with clinical standards.

11. A system for determining levels or concentrations of a substance in a patient's skin based on an optical property of the substance, comprising:
a computing device comprising a memory and a processor;
a software application stored in the memory of the computing device and configured to run on the processor of the computing device; and
a module in communication with the computing device and separated and detached from the computing device, said module comprising:
 a data communication capability, wherein the data includes light intensity or wavelength information;
 a light source that provides light which penetrates the patient's skin to a subcutaneous level;
 a light sensor that detects the light from the light source reflected and scattered from the patient's skin from the subcutaneous level at a single point in time or sequentially at multiple points in time;
 a skin sensor located on the module at a region configured to contact the patient's skin, wherein the skin sensor detects tissue proximity or pressure via a spring-biased electromechanical switch;
 a seal connected to the spring-biased electromechanical switch, wherein the spring-biased electromechanical switch biases the seal to create a light-tight seal on the patient's skin;
 an ambient light sensor; and
 a power source;
wherein the software application is configured to determine the levels or concentrations of the substance in the patient's skin based on a measurement of light intensity or wavelength from the light sensor; and
wherein the skin sensor is configured to determine whether there is a light-tight seal or sufficient pressure between the module and the patient's skin and enable the module to take an optical reading.

12. The system of claim 11, further comprising an indicator light or a visual display activated by the skin sensor to indicate whether there is a light-tight seal or sufficient pressure between the module and the patient's skin.

13. The system of claim 11, wherein the skin sensor is configured to prevent operation or functioning of the system in the absence of a light-tight seal or sufficient pressure between the module and the patient's skin.

14. A system for determining levels or concentrations of a substance in a patient's skin based on an optical property of the substance, comprising:
a computing device comprising a memory, a processor, and a communication capability;
a software application stored in the memory of the computing device and configured to run on the processor of the computing device; and
a module separated and detached from the computing device, said module comprising:
 a data communication capability, wherein the data includes light intensity or wavelength information;
 two or more light sources that provide light which penetrates the patient's skin to a subcutaneous level, wherein the two or more light sources are configured to provide different wavelengths of light sequentially at multiple points in time in rapid succession;
 multiple optical pathways that transmit the light from the two or more light sources that is reflected and scattered from the patient's skin from the subcutaneous level to one or more light sensors that detect the light from the two or more light sources that is reflected and scattered from the patient's skin from the subcutaneous level sequentially at multiple points in time in rapid succession;
 a skin sensor located on the module at a region configured to contact the patient's skin, wherein the skin sensor detects tissue proximity or pressure via a spring-biased electromechanical switch;
 a seal connected to the spring-biased electromechanical switch, wherein the spring-biased electromechanical switch biases the seal to create a light-tight seal on the patient's skin;
 an ambient light sensor; and
 a power source;
wherein the software application is configured to determine the levels or concentrations of the substance in the patient's skin based on a measurement of light intensity or wavelength from the light sensor of the remote module;
wherein the skin sensor is configured to determine whether there is a light-tight seal or sufficient pressure between the module and the patient's skin and enable the module to take an optical reading; and wherein the software application provides reminders to a user to activate the system on a schedule.

15. The system of claim 14, wherein the computing device is a smartphone or a tablet.

16. The system of claim 14, wherein the computing device is a laptop computer or a desktop computer.

17. The system of claim 14, wherein the data communication capability includes BLUETOOTH or other wireless communication.

* * * * *